United States Patent [19]

Lundell et al.

[11] Patent Number: 5,409,816
[45] Date of Patent: Apr. 25, 1995

[54] PROCESS FOR PRODUCING IMMUNOSUPPRESSIVES AND A NOVEL MICROBIAL SPECIES TO BE EMPLOYED THEREIN

[75] Inventors: Juhani Lundell, Raisio; Anja Kopio; Timo Korpela, both of Turku; Matti Ankelo, Uusikaupunki, all of Finland

[73] Assignee: Leiras Oy, Turku, Finland

[21] Appl. No.: 20,545

[22] Filed: Feb. 22, 1993

[30] Foreign Application Priority Data

Dec. 30, 1992 [FI] Finland ................................ 925940

[51] Int. Cl.$^6$ .................... C12P 21/04; C12N 1/14; A61K 37/00; A61K 37/02
[52] U.S. Cl. ................................ 435/713; 435/711; 435/254.1; 514/11; 530/317; 530/321
[58] Field of Search .............. 435/71.3, 254, 71.1; 514/11

[56] References Cited

U.S. PATENT DOCUMENTS

| | | | |
|---|---|---|---|
| 3,878,047 | 4/1975 | Hanka et al. | 435/120 |
| 4,117,118 | 9/1978 | Harri et al. | 424/177 |
| 4,215,199 | 7/1980 | Harri et al. | 435/71 |
| 5,156,960 | 10/1992 | Bokany et al. | 435/71.1 |

FOREIGN PATENT DOCUMENTS

| | | | |
|---|---|---|---|
| 0507968 | 10/1992 | European Pat. Off. | C12P 21/04 |
| 0295870 | 10/1983 | Germany | C12P 21/04 |
| 2227489 | 1/1990 | United Kingdom | C07K 7/64 |
| WO9213094 | 8/1992 | WIPO | C12P 21/04 |

OTHER PUBLICATIONS

Aarnio et al, *Biotech Letters,* 11 (11): 759–764, (1989).
Margaritis et al, *Biotech Letters,* 11 (11): 765–768, (1989).
*ATCC Catalogue of Fungi/Yeasts,* 17th Ed., (1987), pp. 59 and 379.
Isaac et al, *Antimicrobial Agents and Chemotherapy,* vol. 34, pp. 121–127, (Jan. 1990).
Agathos et al, *Ann. N.Y. Acad. Sci.,* 506 (1987) pp. 657–661.
Lee and Agathos, *Biotechnol. Letters* 11 (2) (1989) pp. 77–82.
Aarnio et al, *Appl. Microbiol Biotechnol* (1990) vol. 33, pp. 435–437.
Agathos et al, Journal of Industrial Microbiology, 1 (1986) 39–48, Physiological and genetic factors for process development of cyclosporine fermentations.

*Primary Examiner*—Douglas W. Robinson
*Assistant Examiner*—Maria Luisa Osoteo
*Attorney, Agent, or Firm*—Birch, Stewart, Kolasch and Birch

[57] ABSTRACT

The invention relates to a process for producing a cyclosporin, especially cyclosporin A, by cultivating the strain (LEA3) of the novel Tolypocladium species aerobically at a temperature of 20°–30° C. in a nutrient medium containing carbon sources, nitrogen sources and mineral salts, and, if desired, isolating and purifying the resulting cyclosporin.

4 Claims, No Drawings

PROCESS FOR PRODUCING IMMUNOSUPPRESSIVES AND A NOVEL MICROBIAL SPECIES TO BE EMPLOYED THEREIN

FIELD OF THE INVENTION

The present invention discloses a novel microbial species of Tolypocladium and a process for producing cyclosporins, especially cyclosporin A, by the aerobic fermentation of a strain of this species.

DESCRIPTION OF THE PRIOR ART

Cyclosporins are neutral, highly lipophilic, cyclic undecapeptides with a variable amino acid composition. At present, 25 different forms of cyclosporin (A-Z) are known. The A-form has proved to be clinically the most valuable (Rehácek and De-xiu, Process Biochem. 1991, 26, 157-166).

Originally, cyclosporin was isolated in the 1970's from the fungal strains *Cylindrocarpon lucidum* Booth and *Tolypocladium inflatum* Gams, which had been isolated from soil samples from USA and Norway. The production strain of *Tolypocladium inflatum* (NRRL 8044) was at first identified to be the strain *Trichoderma polysporum* (Link ex Pers) Rifai. The said strain and the antibiotic substances produced thereby are disclosed, for instance, in the FI patent 54606. The growth conditions and the taxonomy of the strain are reported also in the article Dreyfuss et al., Eur. J. Appl. Microbiol., 1976, 3, 125.

The above mentioned strain *Cylindrocarpon lucidum* Booth (NRRL 5760) is disclosed in the FI patent 52851. Other microbial strains producing cyclosporins found in the literature include, for instance, the *Tolypocladium inflatum* strain SF 136 disclosed in the DD patent 298276 producing at least cyclosporin A, and the *Tolypocladium varium* disclosed in the GB patent application No. 2 227 489 producing, a.o. the mixture of cyclosporins A, B and C. In the JP application 826 3093 A2, two strains of Fusarium are disclosed which are mentioned as cyclosporin producing.

In their review article Isaac et al. (Antimicr. Agents Chemoter., 1990, 34, 121-127) compare the cyclosporin production of some known strains of Tolypocladium.

The cyclosporin A was originally discovered as an antifungal antibiotic compound. Its excellent effect as an immunosuppressive was discovered only later (Borel et al., Immunology, 1977, 32, 1017). Thus cyclosporin is currently used in the post-operative treatment of transplantation operations, and it is almost the only medicine for this purpose. This has been reported for the first time in connection with kidney (Calne; Lancet, 1978, 2, 1323) and bone marrow transplantations (Powles, Lancet, 1978, 2, 1327). In addition to transplantation operations, cyclosporin can be used in the treatment of various autoimmune diseases, such as e.g. rheumatism and psoriasis.

The production processes of cyclosporin A by the microbial strains disclosed in the literature have in some cases problems with low yields and long fermentation times. Even if a high yield has been obtained, the relative amount of cyclosporin A has often been small. It has also been shown that the lower yielding strains produce relatively high amounts of cyclosporin A. (De-xiu et al., Folia Microbiol., 1991, 36(6) 549-556).

DESCRIPTION OF THE INVENTION

Our intention was to find a production strain which would give a maximum yield within a short fermentation time and under economical conditions.

While screening for possible production strains, an extremely rapid-yielding strain of Tolypocladium was found which produces considerable amounts of cyclosporin A and relatively small amounts of other forms of cyclosporin, thus allowing for an easier purification of cyclosporin A. The said strain has been isolated from a soil sample originating in Russia, close to Moscow.

When the strain discovered was examined in Holland (W. Gams, Centraalbureau voor Schimmelcultures, Baarn, Holland), the microbe proved to be a representative of a novel species of Tolypocladium. The strain was given the code Tolypocladium sp. LEA3, and the strain has been deposited according to the Budapest Treaty at the depository Centraalbureau voor Schimmelcultures, Oosterstraaf 1, NL-3742 SK Baarn, Holland on Dec. 7, 1992, with the deposition number CBS 630.92.

Thus the invention relates to a novel species of Tolypocladium which gives high yields rapidly, and to its use in the production of the clinically important cyclosporin A.

The genus Tolypocladium was first disclosed by W. Gams in the year 1971 (W. Gams, Persoonia, 1971, vol. 6, part 2, 185-191). Three species of Tolypocladium, *T. inflatum*, *T. geodes* and *T. cylindrosporum*, are studied in the publication. Typically, the species of Tolypocladium are slow in growth, they form white, flocky colonies and a large amount of spores.

The strain Tolypocladium sp. LeA3 according to the present invention was compared to the above mentioned species, and it clearly differed from them by having a weaker spore-forming ability, darker colonies and swollen cell chains. Consequently, the said strain of Tolypocladium was classified as a representative of a new species of Tolypocladium.

The strain Tolypocladium sp. LeA3 according to the invention can be described as follows: A seven-day-old colony on a malt extract/yeast extract plate has a diameter of about 10 mm and is covered by a greyish mycelium which contains few spores. Irregular conidia and swollen cell chains are typical to the strain. As a difference to *Tolypocladium inflatum*, the strain according to the invention does not use raffinose, but is able to use galactose. The growth properties of the strain Tolypocladium sp. LeA3 compared to the properties of *Tolypocladium inflatum* and *Cylindrocarpon lucidum* are summarized in the Table I.

TABLE I

The use of carbon sources of the microbial strains

| Carbon source | Strain | | |
|---|---|---|---|
| | 25 A | 51 | 52 |
| GLU | + | + | + |
| GLY | + | + | + |
| 2KG | + | + | + |
| ARA | + | + | + |
| XYL | + | + | + |
| ADO | + | + | − |
| XLT | + | + | − |
| GAL | + | − | + |
| INO | + | + | + |
| SOR | + | + | + |
| MDG | − | − | + |
| NAG | + | + | + |
| CEL | + | + | + |

TABLE I-continued

The use of carbon sources of the microbial strains

| Carbon source | Strain | | |
|---|---|---|---|
| | 25 A | 51 | 52 |
| LAC | − | − | + |
| MAL | + | + | + |
| SAC | + | + | + |
| TRE | + | + | + |
| MLZ | + | + | + |
| RAF | − | + | + |

The cultivation time was 4 d.
25A=Tolypocladium sp. LeA3
51=Tolypocladium inflatum
52=Cylindrocarpon lucidum In the process according to the present invention, for the production of cyclosporins, especially cyclosporin A, a strain of the novel Tolypocladium species, or a strain derived therefrom, is cultivated aerobically at a temperature of 20°-30° C. in a growth medium, which contains carbon sources, nitrogen sources and mineral salts, and, if desired, the resulting cyclosporins are isolated and purified.

DESCRIPTION OF THE PREFERRED EMBODIMENTS

In a preferred method according to the invention the strain Tolypocladium sp. LeA3 CBS 630.92 is used. The strain is especially preferable for the purposes of the invention, since it produces great amounts of cyclosporins already after a few days of cultivation. Besides, it produces a proportionally large amount of cyclosporin A. Although the strain produces also other forms of cyclosporin (B, C, D and G), the amount of these is considerably lower than that of most of the known strains (see Isaac et al., supra). The strain produces the C-form only 10%, the B-form 4% and the D and G forms together 2%. This is the case in spite of the fact that the production of the A-form is high, even 1.5 g/l.

The above mentioned strain according to the invention is advantageous also in that it grows rapidly and in very conventional growth media. The strain is able to use, for instance, glucose, sucrose, arabinose, xylose and galacrose (see Table I) as carbon sources, as well as several both organic and inorganic nitrogen sources, such as peptone, soya meal, fish meal, cottonseed meal and $(NH_4)_2SO_4$.

In addition to these, the nutrient media used usually contain mineral salts, such as magnesium sulphate or potassium dihydrogen phosphate.

Preferably, moderately priced molasses can be used as a carbon source and soya meal as a nitrogen source.

In a preferred method according to the invention, a spore and mycelium inoculum is inoculated into a precultivation medium, which inoculum has been obtained by suspending in water a culture collected from a slope of Tolypocladium sp. LEA3. The culture is precultivated for 2-4 days and the production medium is inoculated with the precultivation broth. The actual cultivation is performed at a temperature of about 20 to about 30° C., preferably 25°-30° C., particularly at 25° C. for 5-7 days, maintaining the pH of the culture between 3-8, preferably between 4-7 by adding 1M NaOH or 1M HCl, if necessary.

The aerobic conditions are maintained by aerating for example 1 vol/min (a volume of air corresponding to that of the culture per minute), and the culture is stirred at the rate of 200-350 rpm.

During the fermentation the amounts of cyclosporin are monitored with high performance liquid chromatography (HPLC), as for instance Isaac et al. (supra) have described. The fermentation is continued until a maximum amount of cyclosporins has been formed. The strain according to the invention produces cyclosporin A up to 1500 mg/l within six days, the relative proportion of cyclosporin A being up to 84%.

The mixture of cyclosporin forms can be isolated and purified by conventional methods. The mycelium is separated from the culture broth either by filtration or centrifugation. The cyclosporins are extracted from the mycelium with a lower alkanol, for example methanol, ethanol or isopropanol, preferably methanol. The extract is concentrated and reextracted with a water-insoluble organic solvent, for example butyl or ethyl acetate, preferably ethyl acetate. The evaporation residue of the extract obtained is dissolved in a suitable organic solvent, for example toluene, and cyclosporin A is separated with column chromatography, for example in a silica gel column. The fractions containing the desired cyclosporin A are analyzed by means of thin layer chromatography, the fractions are concentrated and cyclosporin A is recrystallized from a suitable solvent or a mixture of solvents, for example ether-hexane.

Finally, the product obtained is characterized, for example, by determining its melting point and optical rotation.

The following examples illustrate the invention further.

Example 1

A spore and mycelium inoculum was made from a slope of Tolypocladium sp. LeA3 by suspending the culture in 5 ml of sterile water. 1 ml of this suspension was used to inoculate 50 ml of the nutrient medium (E1) in a 250 ml erlenmeyer flask.

The composition of the precultivation medium E1

| glucose | 30 g |
|---|---|
| soya meal | 15 g |
| potassium dihydrogen phosphate | 1 g |
| magnesium sulphate | 0.5 g |
| ammonium sulphate | 5 g |
| $H_2O$ | ad 1 l |

The mixture was sterilized for 20 min at 121° C.

The culture was incubated at 25° C. on a shaker (340 rpm) for 2 d after which the precultivation broth (50 ml) was transferred in sterile conditions into 5 l of the production medium (T1) in a 10 l fermentor.

The composition of the production medium T1

| molasses | 150 g |
|---|---|
| soya meal | 17 g |
| ammonium sulphate | 5 g |
| potassium dihydrogen phosphate | 1 g |
| magnesium sulphate | 0.5 g |
| $H_2O$ | ad 1 l |

The mixture was sterilized for 20 min at 121° C.

The cultivation was performed at 25° C., aeration 1 vol/min, stirring rate 200 rpm. The amounts of cyclosporin in the cultivation medium were monitored throughout the cultivation with HPLC (Isaac et al., supra). The fermentation was continued for 144 hours, whereupon the concentration of cyclosporin A was 1500 mg/l. The concentrations of the other forms were as follows: C: 155 mg/l, B: 62 mg/l, D: 28 mg/l and G: 29 mg/l.

The mixture of cyclosporin forms was isolated and purified as follows: 4.5 l of the fermentation broth was filtered and the culture was extracted twice with 1 l of methanol. The extracts were pooled and concentrated under vacuum. From the residue, the cyclosporins were extracted twice with 300 ml of ethyl acetate. The ethyl acetate solutions were combined and dried with sodium sulphate. The solution was further concentrated and the residue was dissolved in 100 ml of toluene. The solution was applied onto a column (5 cm×40 cm) filled with 200 g of silica gel (Merck, 0.063–0.2 mm) in toluene. The column was eluted with a mixture containing toluene and acetone in a proportion of 4:1. The fractions containing pure cyclosporin A were collected for the further treatment (analysis with TLC, plate Kieselgel 60 F 254, developing solution hexane/acetone 1:1, detection with iodine vapour). The pooled fractions were concentrated and cyclosporin A was crystallized from ether-hexane. The yield was 4.5 g. The mp. of cyclosporin A was 139°–140 ° C. and optical rotation −189° (0.5 MeOH).

Example 2

The spore and mycelium inoculum was made as in the Example 1. 1 ml of this suspension was used to inoculate 50 ml of the nutrient medium (E2) in a 200 ml erlenmeyer flask.

The composition of precultivation medium E2

| maltose | 40 g |
| ammonium sulphate | 5 g |
| cottonseed meal | 10 g |
| potassium dihydrogen phosphate | 1 g |
| magnesium sulphate | 0.5 g |
| $H_2O$ | ad 1 l |

The mixture was sterilized for 20 min at 121° C.

The culture was incubated at 25 ° C. on a shaker (230 rpm) for 2 d, after which the precultivation solution (50 ml) was transferred in sterile conditions into 5 l of the production medium (T2) in a 10 l fermentor.

The composition of the production medium T2:

| glucose | 10 g |
| maltose | 10 g |
| sucrose | 60 g |
| cottonseed meal | 10 g |
| cottonseed oil | 5 g |
| ammonium sulphate | 5 g |
| potassium dihydrogen phosphate | 1 g |
| magnesium sulphate | 0.5 g |
| $H_2O$ | ad 1 l |

The mixture was sterilized for 20 min at 121° C.

The cultivation was performed at 24° C., aeration 1 vol/min, stirring rate 200 rpm. The fermentation was continued for 120 hours, whereupon the concentration of cyclosporin A was 1410 mg/l. The amounts of cyclosporin in the culture solution were monitored throughout the cultivation with HPLC (Isaac et al., supra). The concentrations of the other forms were as follows: C: 135 mg/l, B: 50 mg/l, G and D: 30 mg/l.

Cyclosporin A was purified as in the Example 1.

DEPOSITED MICROORGANISMS

The following microorganism was deposited according to the Budapest Treaty at the depository Centraalbureau voor Schimmelcultures (CBS), Oosterstraat 1, NL-3742 SK Baarn, Holland

| Microorganism | Deposition number | Deposition date |
| --- | --- | --- |
| Tolypocladium sp. LeA3 | CBS 630.92 | December 7, 1992 |

We claim:

1. A process for producing cyclosporin A, comprising culturing a strain having all of the identifying characteristics of Tolypocladium species LeA3 CBS 630.92, in a nutrient medium comprising molasses and soya meal, or sucrose and cottonseed mean, until said cyclosporin A is produced, and recovering said cyclosporin A so produced.

2. The process according to claim 1, wherein said culturing is conducted aerobically at a temperature of 20°–30 ° C.

3. The process according to claim 1, wherein said strain is Tolypocladium sp. LeA3 CBS 630.92.

4. A biologically pure culture of Tolypocladium sp. LeA3 having the deposit number CBS 630.92.

* * * * *